United States Patent
Wegener et al.

(10) Patent No.: US 10,865,805 B2
(45) Date of Patent: Dec. 15, 2020

(54) FLEXIBLE IMPELLER PUMPS AND DISPOSABLE FLUID FLOW CIRCUITS INCORPORATING SUCH PUMPS

(71) Applicant: Fenwal, Inc., Lake Zurich, IL (US)

(72) Inventors: Christopher J. Wegener, Libertyville, IL (US); Mark J. Brierton, Cary, IL (US)

(73) Assignee: Fenwal, Inc., Lake Zurich, IL (US)

( * ) Notice: Subject to any disclaimer, the term of this patent is extended or adjusted under 35 U.S.C. 154(b) by 496 days.

(21) Appl. No.: 15/643,526

(22) Filed: Jul. 7, 2017

(65) Prior Publication Data

US 2018/0010612 A1    Jan. 11, 2018

Related U.S. Application Data

(60) Provisional application No. 62/359,914, filed on Jul. 8, 2016.

(51) Int. Cl.
| | | |
|---|---|---|
| *F04D 29/30* | (2006.01) |
| *A61M 1/10* | (2006.01) |
| *A61M 1/26* | (2006.01) |
| *A61M 1/30* | (2006.01) |
| *F04D 13/02* | (2006.01) |
| *F04D 29/043* | (2006.01) |
| *F04D 29/42* | (2006.01) |

(52) U.S. Cl.
CPC ......... *F04D 29/305* (2013.01); *A61M 1/1037* (2013.01); *A61M 1/267* (2014.02); *A61M 1/301* (2014.02); *F04D 13/024* (2013.01); *F04D 29/043* (2013.01); *F04D 29/4293* (2013.01)

(58) Field of Classification Search
CPC .. F04D 29/305; F04D 29/4293; F04D 13/024; F04D 29/043; A61M 1/1037; A61M 1/267; A61M 1/301
See application file for complete search history.

(56) References Cited

U.S. PATENT DOCUMENTS

| | | |
|---|---|---|
| 2,933,046 A | 4/1960 | McCray |
| 3,054,355 A | 9/1962 | Neely |

(Continued)

FOREIGN PATENT DOCUMENTS

| | | |
|---|---|---|
| GB | 954139 | 4/1964 |
| NL | 1007880 C1 | 6/1999 |
| WO | WO 99/66208 A1 | 12/1999 |

OTHER PUBLICATIONS

Extended European Search Report for Application No. EP17180160.8 dated Nov. 16, 2017.

*Primary Examiner* — Eldon T Brockman
(74) *Attorney, Agent, or Firm* — Cook Alex Ltd.

(57) ABSTRACT

A disposable fluid pump is provided with a housing including first and second faces, with a sidewall extending between the first and second faces. The housing defines a chamber, with an inlet and an outlet in fluid communication with the chamber. An impeller is rotatably mounted within the chamber and includes a plurality of flexible vanes. Such a pump may be incorporated into a disposable fluid flow circuit that is adapted to be mounted on a durable hardware for processing a fluid. In such a fluid flow circuit, the fluid pump may be integrated into a cassette of the circuit or, alternatively, the inlet and outlet of the fluid pump may be directly connected to fluid flow conduits of the circuit.

21 Claims, 10 Drawing Sheets

(56) References Cited

U.S. PATENT DOCUMENTS

| | | | | |
|---|---|---|---|---|
| 3,202,103 | A | | 8/1965 | Sully |
| 3,626,265 | A | * | 12/1971 | Kraakman ............ F04C 2/3446 418/266 |
| 3,832,105 | A | | 8/1974 | Takahashi |
| 4,435,138 | A | * | 3/1984 | Johnson ................ F01C 1/3441 418/131 |
| 4,898,518 | A | | 2/1990 | Hubbard et al. |
| 5,393,207 | A | | 2/1995 | Maher et al. |
| 5,496,159 | A | * | 3/1996 | Devore ................ F01C 21/104 418/178 |
| 5,614,106 | A | | 3/1997 | Payrat et al. |
| 5,868,696 | A | | 2/1999 | Giesler et al. |
| 6,210,133 | B1 | * | 4/2001 | Aboul-Hosn ........... F04D 13/06 417/423.1 |
| 8,096,530 | B2 | | 1/2012 | Pelfrey |
| 8,157,510 | B2 | * | 4/2012 | Bear ........................ F04C 5/00 415/141 |
| 9,044,535 | B2 | | 6/2015 | Garzaniti et al. |
| 9,719,508 | B2 | * | 8/2017 | Salmela ..................... F04C 5/00 |
| 10,029,038 | B2 | * | 7/2018 | Hodges ................ A61M 1/1013 |
| 10,183,103 | B2 | * | 1/2019 | Wiktor .................. A61M 1/101 |
| 2006/0051217 | A1 | | 3/2006 | Felton |
| 2006/0278657 | A1 | | 12/2006 | Roatis |
| 2009/0180879 | A1 | * | 7/2009 | Bear ........................ F04C 5/00 416/132 R |
| 2013/0004357 | A1 | * | 1/2013 | Sexton .................... F04C 15/06 418/259 |
| 2014/0301833 | A1 | * | 10/2014 | Salmela ..................... F04C 5/00 415/168.1 |
| 2014/0369824 | A1 | * | 12/2014 | Guo .................... F04D 29/4273 415/204 |
| 2016/0067394 | A1 | * | 3/2016 | Wiktor .................. A61M 1/101 415/203 |
| 2017/0021069 | A1 | * | 1/2017 | Hodges ............... A61M 1/1036 |
| 2017/0302145 | A1 | * | 10/2017 | Holenstein ........... H02K 19/103 |

* cited by examiner

FLEXIBLE IMPELLER PUMPS AND DISPOSABLE FLUID FLOW CIRCUITS INCORPORATING SUCH PUMPS

CROSS REFERENCE TO RELATED APPLICATIONS

This application claims the benefit of and priority of U.S. Provisional Patent Application Ser. No. 62/359,914, filed Jul. 8, 2016, the contents of which are incorporated by reference herein.

BACKGROUND

Field of the Disclosure

The present subject matter relates to impeller pumps for moving fluid through a fluid flow circuit. More particularly, the present subject matter relates to flexible impeller pumps for use in disposable fluid flow circuits.

Description of Related Art

A variety of systems and methods are known for pumping or otherwise moving fluid through a fluid flow path, with the most preferable method for moving fluid through a fluid flow path depending on a number of factors. For example, extracorporeal processing of bodily fluid (e.g., blood withdrawal and separation or peritoneal dialysis) may involve any of a number of fluid movement techniques and devices. According to one approach, a durable processing system or device is used in combination with a disposable processing set or circuit. The durable processing system typically includes a pump assembly that interacts with one or more of the components of the disposable circuit to draw blood or another bodily fluid from a patient or donor or subject and then move the blood or bodily fluid to another location within the disposable circuit, which may include returning or all of portion of the blood or bodily fluid to the patient or donor or subject.

Frequently, the component of the disposable circuit that interacts with the pump assembly is a molded plastic piece commonly referred to as a cassette. As used herein, the term "cassette" refers to a component of a fluid processing system that includes one or more defined fluid passageways. The cassette is secured to a cassette holder or cassette station of the durable equipment, with a flexible membrane or diaphragm or sheet of the cassette facing the durable equipment. The cassette holder or cassette station typically includes a number of valve actuators that selectively press against the flexible diaphragm for opening and closing valve stations of the cassette, thereby controlling which of the fluid passageways are connected to each other and directing the fluid between any of a number of sources and destinations.

An exemplary cassette and cassette holder are employed by the AMICUS® system sold by Fenwal, Inc. of Lake Zurich, Ill., which is an affiliate of Fresenius Kabi AG of Bad Homburg, Germany. One version of the AMICUS® system is described in greater detail in U.S. Pat. No. 5,868,696, which is hereby incorporated herein by reference. In the AMICUS® system, fluid flow is controlled by a disposable cassette with preformed fluid passages, which interfaces with an array of actuators and sensors located on a panel of the durable hardware. Flexible tubing loops connected to opposing edges of the cassette are received within peristaltic pump stations having rollers that press against the loops and rotate to move fluid through the cassette (and through the other components of the disposable circuit).

According to another approach, a reusable hardware system is configured to be used in combination with a disposable fluid flow circuit omitting a cassette. The Autopheresis-C® system sold by Fenwal, Inc. of Lake Zurich, Ill., which is an affiliate of Fresenius Kabi of Bad Homburg, Germany, is exemplary of such an approach. One version of the Autopheresis-C® system is described in greater detail in U.S. Pat. No. 5,614,106, which is hereby incorporated herein by reference. In such a system, rather than peristaltic pumps engaging tubing loops extending from the edges of a cassette, the disposable fluid flow circuit includes a plurality of flexible tubes or fluid flow conduits that may be associated with peristaltic pumps of the durable hardware, which are actuated to cause fluid flow through the circuit.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a disposable fluid pump is provided with a housing including first and second faces, with a sidewall extending between the first and second faces. The housing defines a chamber, with an inlet and an outlet in fluid communication with the chamber. An impeller is rotatably mounted within the chamber and includes a plurality of flexible vanes.

In another aspect, a disposable cassette is adapted for incorporation into a disposable fluid flow circuit. The disposable cassette includes a body with a topside, an underside, and an edge wall extending therebetween. The body defines a plurality of fluid flow paths. The cassette also includes a fluid pump associated with the body and including a housing with first and second faces and a sidewall extending therebetween. The housing defines a chamber, with an inlet and an outlet each in fluid communication with the chamber and with a different one of the fluid flow paths defined by the body. The fluid pump further includes an impeller rotatably mounted within the chamber, which includes a plurality of flexible vanes.

In yet another aspect, a disposable fluid flow circuit is adapted for cooperative mounting on a durable hardware for processing a fluid. The disposable fluid flow circuit includes a plurality of fluid flow conduits and a fluid pump. The fluid pump is operable to convey fluid through at least a portion of the fluid flow circuit and includes a housing with first and second faces and a sidewall extending therebetween. The housing defines a chamber, with an inlet and an outlet in fluid communication with the chamber. An impeller is rotatably mounted within the chamber and includes a plurality of flexible vanes.

DESCRIPTION OF THE ILLUSTRATED EMBODIMENTS

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

Figure 1:
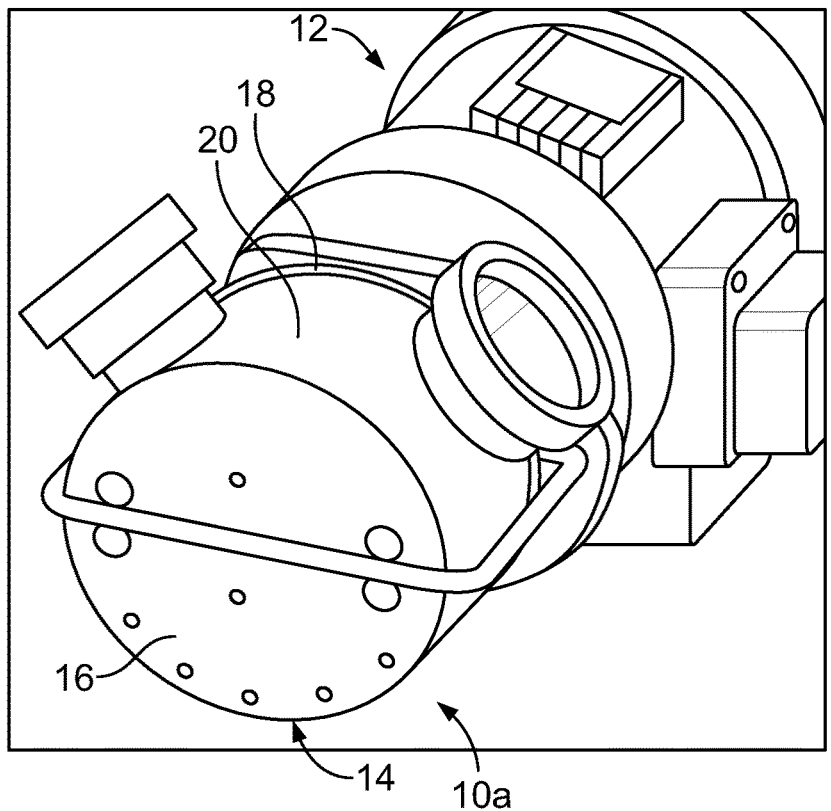
FIG. 1 is a front perspective view of an exemplary disposable fluid pump and durable drive unit according to an aspect of the present disclosure.

FIG. 1 shows an exemplary embodiment of a disposable fluid pump 10a of a disposable fluid flow circuit (not illustrated) in operative association with a durable drive unit 12 of a durable hardware (not illustrated) onto which the fluid flow circuit may be mounted for fluid processing. Several variations of disposable fluid pumps will be described herein (collectively identified by the reference numeral 10), being differently configured and/or operating in different ways. It should be understood that the configurations and operative principles of the various fluid pumps described herein may be combined and otherwise modified, with one or more individual aspects of a particular fluid pump being applicable to modify the configuration and/or operation of another one of the fluid pumps described herein. Additionally, to the extent not explicitly described (and not contradicted by explicit disclosure), it should be understood that the components of the various fluid pumps described herein, along with the operation of the individual components and structure and operation of the fluid pump as a whole, are in accordance with the detailed description of a corresponding component of any other fluid pump described herein or of the overall structure and operation of any other fluid pump described herein.

The fluid pump 10a comprises a housing 14 including a first or front face 16 and a second or rear face 18, with a sidewall 20 extending between the first and second faces 16 and 18. As used herein, the term "face" refers to the surface or surfaces of the housing 14 through which a rotational axis A of an impeller 22 positioned within the housing 14 extends (FIG. 2), while the "sidewall" is the surface or surfaces connecting the "faces" and typically extends in a direction generally parallel to the rotational axis A of the impeller 22. In one embodiment, the housing 14 is formed of a generally rigid, disposable material, with faces 16 and 18 that are substantially parallel and a sidewall 20 that is generally perpendicular to the faces 16 and 18. It should be understood that the configuration of the housing 14 of FIG. 1 is merely exemplary and that the housing 14 of a fluid pump 10 according to the present disclosure may be differently configured.

The housing 14 defines a cavity or chamber 24 (FIG. 2), with an inlet 26 and an outlet 28 in fluid communication with the chamber 24. Each of the inlet 26 and the outlet 28 is configured to allow fluid flow between the chamber 24 of the fluid pump 10a and a location positioned externally of the fluid pump 10a. For example, a fluid conduit or flexible tubing may be connected to the inlet 26 to allow the fluid pump 10a to draw fluid through the conduit and into the chamber 24 via the inlet 26, as will be described in greater detail. Similarly, a second fluid conduit or flexible tubing or the like may be connected to the outlet 28 to allow the fluid pump 10a to expel or convey fluid out of the chamber 24 and into the second conduit via the outlet 28, as will be described in greater detail.

Figure 2:
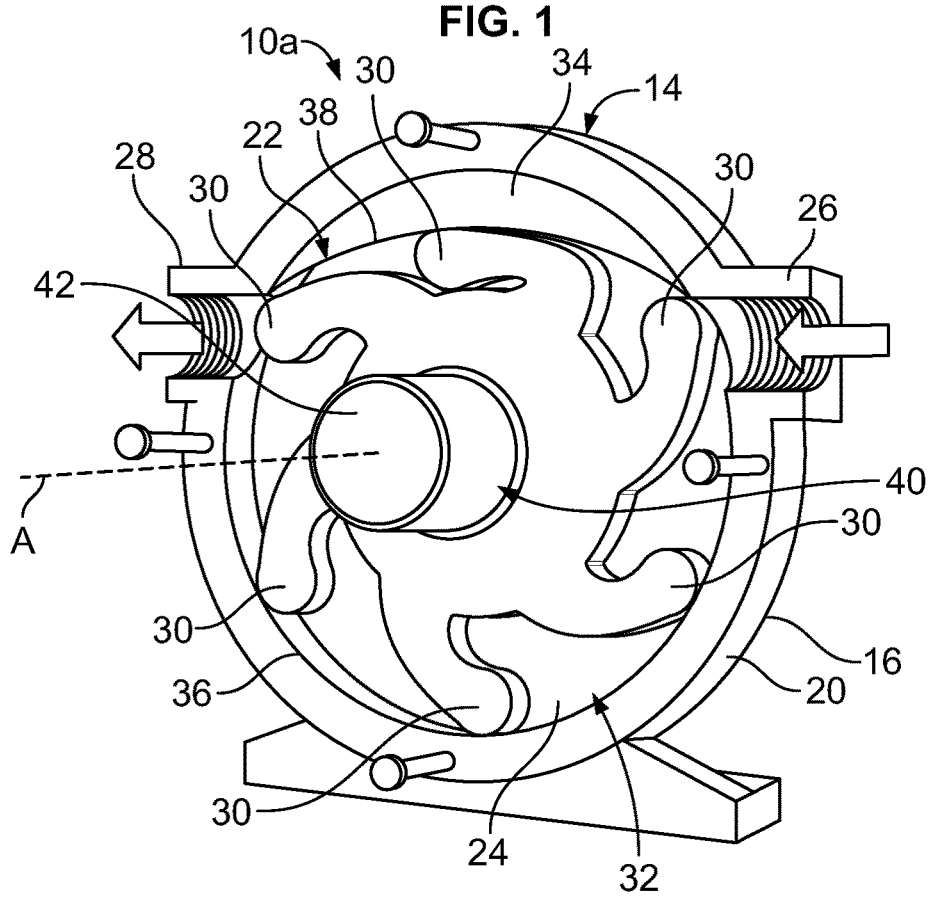
FIG. 2 is a rear perspective view of the disposable fluid pump of FIG. 1, with portions of the disposable fluid pump broken away for illustrative purposes.

In the embodiment of FIGS. 1 and 2, each of the inlet 26 and outlet 28 extends through the sidewall 20 to allow fluid flow between the chamber 24 and a position that is external to the chamber 24. In other embodiments, one or both of the inlet 26 and outlet 28 may extend from the chamber 24 to one of the housing faces 16, 18. Regardless of the exact position of the inlet 26 and the outlet 28, it may be advantageous for them to be positioned apart from each other, rather than being directly adjacent to each other. For example, in the embodiment of FIGS. 1 and 2, the inlet 26 and outlet 28 are positioned approximately 90° apart about the rotational axis A of the impeller 22 mounted within the chamber 24. In other embodiments in which the inlet 26 and outlet 28 each extend through the sidewall 22 of the housing 14, the inlet 26 and outlet 28 may be positioned more or less than 90° apart about the rotational axis A.

FIG. 2 shows an exemplary impeller 22 that may be at least partially positioned within the chamber 24 defined by the pump housing 14. To that end, it may be advantageous for the housing 14 to be provided in two or more pieces, which allows the impeller 22 to be positioned in the portion of the chamber 24 defined by one of the housing pieces while the fluid pump 10a is in a partially assembled condition (as in FIG. 2), with additional pieces of the housing 14 being subsequently secured to the first housing piece to fully define the housing 14 and at least partially enclose the impeller 22 within the chamber 24 (FIG. 1).

Figure 4:
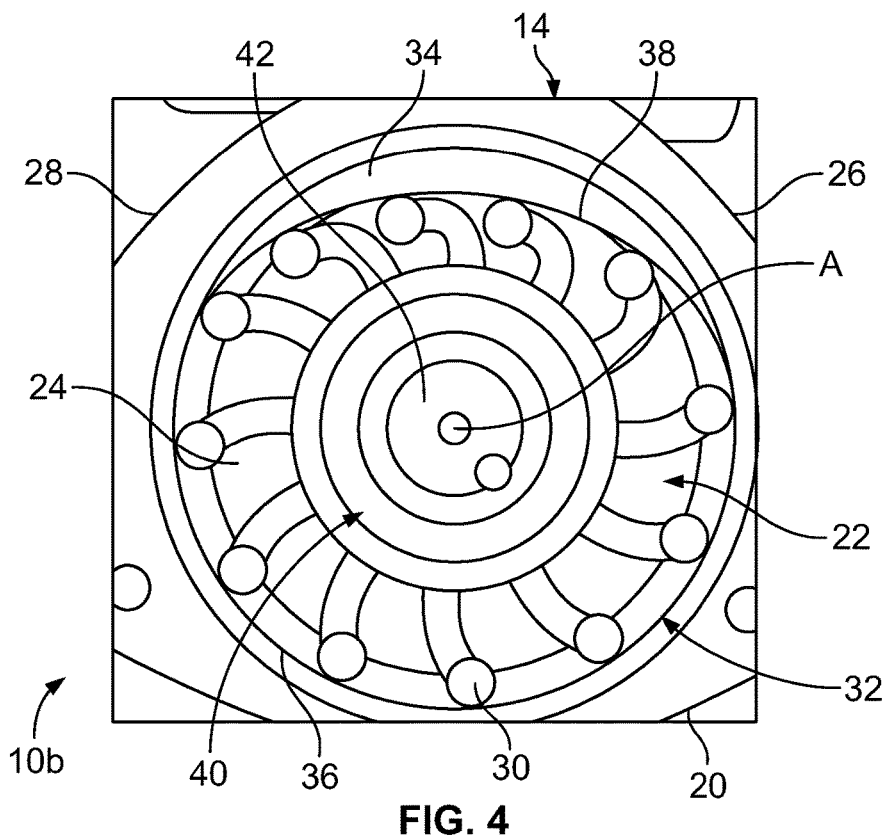
FIG. 4 is a plan view of another embodiment of a disposable fluid pump according to an aspect of the present disclosure, with portions of the disposable fluid pump broken away for illustrative purposes.

The impeller 22 is rotatably mounted within the chamber 24 to allow the impeller 22 to rotate about a rotational axis A, which may coincide with the central axis or midpoint of the impeller 22. The impeller 22 includes a plurality of flexible vanes or blades 30. In the embodiment of FIG. 2, the impeller 22 includes six substantially identical vanes 30, but it is within the scope of the present disclosure for an impeller to include more or fewer than six vanes (see the fluid pump 10b of FIG. 4, for example) and/or for the individual vanes of an impeller to be differently configured than the individual vanes 30 of FIG. 2. It is also within the scope of the present disclosure for two or more vanes of a particular impeller to be differently configured from each other. Preferably, each vane 30 is equally spaced from each adjacent vane 30 (e.g., with there being a 60° separation between adjacent vanes of an impeller having six vanes), but it is also within the scope of the present disclosure for the angle between adjacent vanes of a single impeller to vary.

Each vane 30 is preferably sufficiently elongated so as to contact the perimeter wall 32 of the chamber 24 (which is defined by the sidewall 20 of housing 14 in the embodiment of FIGS. 1 and 2). Thus, as the impeller 22 rotates within the chamber 24, a portion of each vane 30 slides along the perimeter wall 32 of the chamber 24. Preferably, the impeller 22 and each vane 30 is also sufficiently tall or thick to extend between the upper and lower ends of the chamber 24 (which may be defined by the housing faces 16 and 18), such that fluid positioned between a pair of adjacent vanes 30 cannot move beyond or around either vane and must remain between the vanes until exiting the chamber 24 via the outlet 28 (as will be described).

Figure 3:
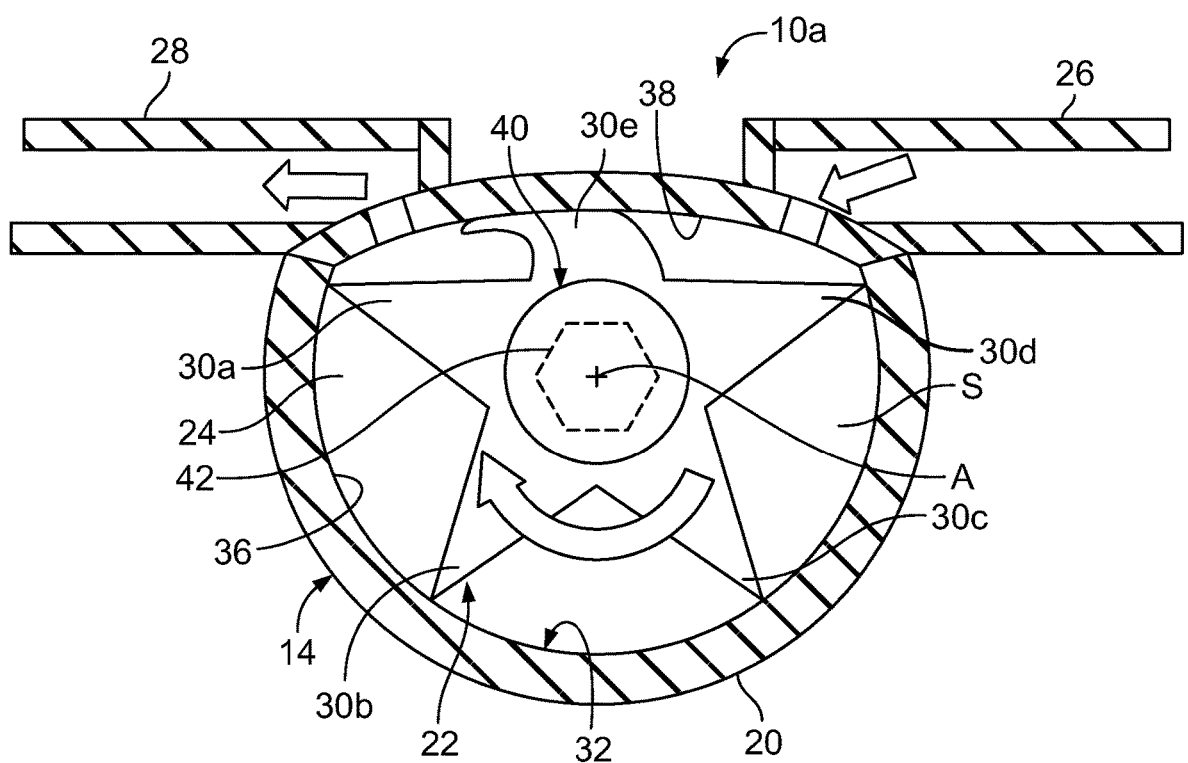
FIG. 3 is a diagrammatic view of the disposable fluid pump of FIG. 1, showing fluid flow into and out of the chamber of the disposable fluid pump.

As will be described in greater detail, the chamber 24 is preferably non-circular, with a non-uniform diameter, in which case the distance between the perimeter wall 32 and the rotational axis A varies at different angular positions about the rotational axis A. By providing vanes 30 that are formed of a flexible material or materials, the shape of each vane 30 may resiliently deform during rotation of the impeller 22 to occupy the appropriate space between the rotational axis A and the portion of the perimeter wall 32 contacted by the vane 30. Thus, at angular positions at which the perimeter wall 32 is spaced relatively far from the rotational axis A, a vane 30 may be in an unflexed or less flexed condition (see vanes 30a-30d of FIG. 3), whereas a vane may be in a flexed or more flexed condition (see vane 30e of FIG. 3) at angular positions at which the perimeter wall 32 is spaced relatively close to the rotational axis A. When transitioning between its least (or unflexed) and most flexed conditions, each vane 30 passes through partially flexed conditions, with the instantaneous shape and degree of flexure of the vane 30 depending upon its angular position (which is determinative of the distance between the rotational axis A and the perimeter wall 32).

Turning back now to the chamber 24 illustrated in FIG. 2, a generally crescent-shaped surface or structure or formation 34 is associated with a portion of the sidewall 20. Due to the presence of the generally crescent-shaped formation 34 (which may be integrally formed with the housing 14 or separated provided and positioned within the chamber 24), the perimeter wall 32 has a non-uniform radius about the rotational axis A of the impeller 22. In the embodiment of FIG. 2, the housing sidewall 20 defines a perimeter wall 32 and chamber 24 with a high-radius arc or portion 36 and a low-radius arc or portion 38. The high- and low-radius portions 38 and 36 are separated by the inlet and outlet 26 and 28, with the high-radius portion 36 having a greater angular extent (approximately 270°) than the low-radius portion 38 (approximately 90°). In the high-radius portion 36, the perimeter wall 32 may be substantially concentric with the rotational axis A of the impeller 22 or, stated differently, have an at least substantially uniform radius from the rotational axis A. In the illustrated low-radius portion 38 (which coincides with the generally crescent-shaped formation 34), the perimeter wall 32 has a radius (which may be either uniform or non-uniform) that is preferably no greater than the radius of the perimeter wall 32 in the high-radius portion 36. In the illustrated embodiment, the radius of the perimeter wall 32 at the ends of the low-radius portion 38 may be substantially equal to the radius of the perimeter wall 32 in the high-radius portion 36 (i.e., at the transition points between the high- and low-radius portions 36 and 38), while the radius of perimeter wall 32 is smaller at all other points of the low-radius portion 38. In other embodiments, the perimeter wall 32 may have some other profile, including a non-uniform radius in the high-radius portion and/or high- and low-radius portions that occupy different angular extents than the high- and low-radius portions 36 and 38 of FIG. 2.

The varying radius of the perimeter wall 32 and the ability of the vanes 30 to flex allows for fluid flow into, through, and out of the chamber 24. The inlet 26 and outlet 28 are positioned at the transition points between the high- and low-radius portions 36 and 38 of the perimeter wall 32. At these transition points, a vane 30 will be forced to flex from a less flexed condition to a more flexed condition (when being rotated from the high-radius portion 36 of the chamber 24 into the low-radius portion 38) or from a more flexed condition to a less flexed condition (when being rotated from the low-radius portion 38 of the chamber 24 into the high-radius portion 36). Changing the configuration of a vane 30 affects the volume of the space S (FIG. 3) between that vane 30 and its trailing vane 30 (i.e., the vane 30 that rotates through a transition point immediately after the vane 30 that has just been rotated through the transition point). When a vane 30 is rotated into the low-radius portion 38 (i.e., at the transition point that coincides with the position of the outlet 28), it will move to a more flexed condition that places it closer to its trailing vane 30, thereby decreasing the volume of the space S therebetween. By decreasing the volume of this space S at the outlet 28, the two vanes 30 force the fluid within the space S therebetween to move out of the space S, exiting the chamber 24 via the outlet 28. Conversely, when a vane 30 is rotated into the high-radius portion 36 (i.e., at the transition pint that coincides with the position of the inlet 26), it will move to a less flexed condition that places it farther from its trailing vane 30, thereby increasing the volume of the space S therebetween. By increasing the volume of this space S at the inlet 26, the two vanes 30 create a vacuum, which draws fluid through the inlet 26 and into the space S.

Accordingly, due to the flexibility of the impeller vanes 30 and the configuration of the chamber 24, rotation of the impeller 22 within the chamber 24 draws fluid into the chamber 24 via the inlet 26, transports the fluid through the chamber 24 from the inlet 26 to the outlet 28 between an adjacent pair of rotating vanes 30, and then expels the fluid from the chamber 24 via the outlet 28. The rate at which fluid is pumped into and out of the fluid pump 10a and/or the volume of fluid drawn into and expelled from the chamber 24 at each stroke (which may be defined as the moment at which the configuration of a vane 30 changes upon moving through a transition point) may be controlled in part by selection of a suitably configured fluid pump prior to beginning a fluid processing procedure. Once such a procedure has begun, the rate of rotation of the impeller 22 may be varied to change the volumetric flow rate of fluid through the fluid pump 10a. It should be understood that reversing the rotational direction of the impeller 22 reverses the flow of fluid through the fluid pump 10a, with fluid entering the chamber 24 via the outlet 28 and exiting the chamber 26 via the inlet 26. The chamber 24 may be either symmetrically configured or asymmetrically configured, depending on whether it is preferred for the nature of fluid flow through the fluid pump 10a to be the same in both directions or to be direction-dependent.

As for the mechanism or device that causes rotation of the impeller 22, its structure may vary without departing from the scope of the present disclosure. In the embodiment of FIGS. 1 and 2, the impeller 22 includes a rigid hub 40 (FIG. 2), which may be formed of a material that is less flexible than the vanes 30 (e.g., a substantially rigid plastic or metallic material). The rigid hub 40 is a central component of the impeller 22, with the vanes 30 extending outwardly from the rigid hub 40. When the impeller 22 is mounted within the housing chamber 24, the rigid hub 40 may be positioned at and define the rotational axis A.

Figure 5:
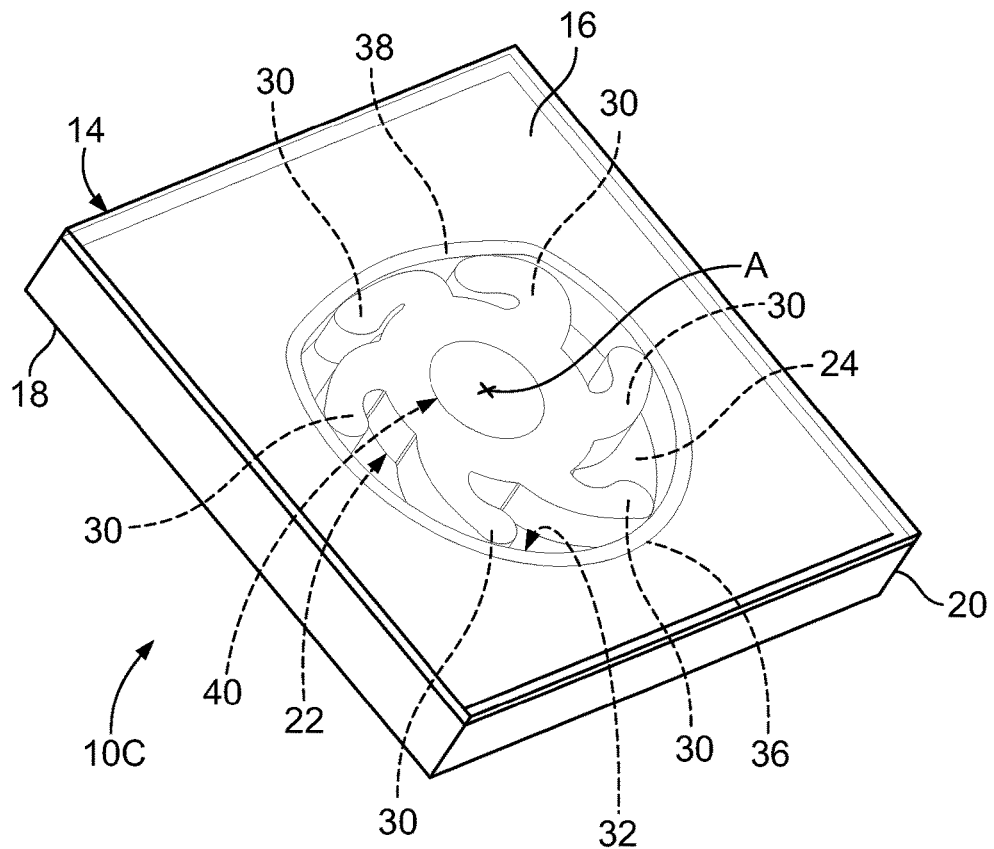
FIGS. 5 and 6 are perspective views of another embodiment of a disposable fluid pump according to an aspect of the present disclosure.
Figure 7:
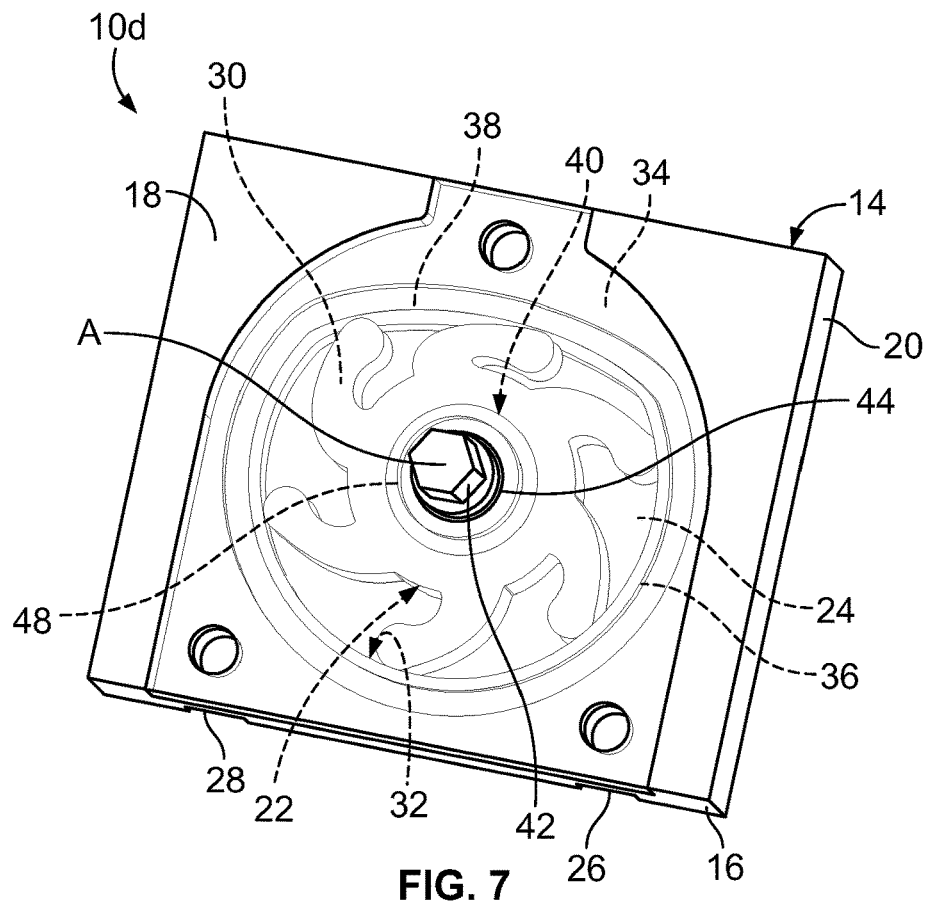
FIGS. 7 and 8 are perspective views of another embodiment of a disposable fluid pump according to an aspect of the present disclosure.
Figure 8:
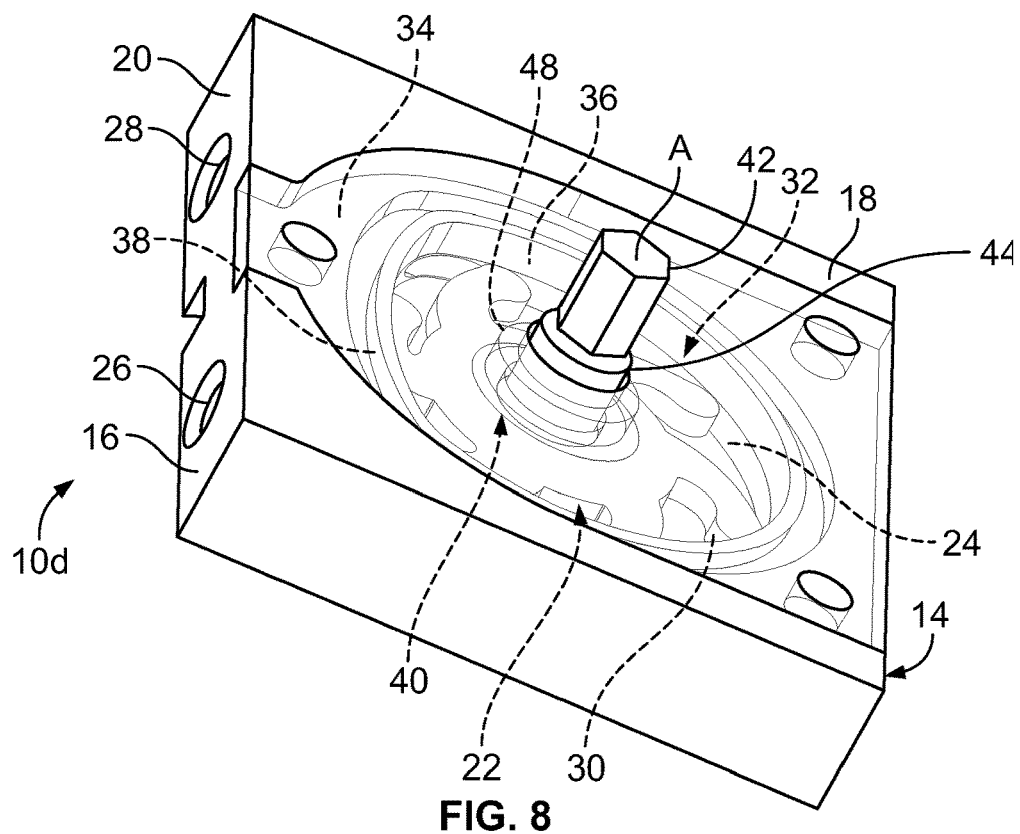

The rigid hub 40 of FIG. 2 includes a shaft portion 42 that extends outside of the chamber 24, through an opening defined in one of the housing faces 16, 18. This same type of rigid hub 40 and shaft portion 42 is employed in the embodiment of FIGS. 5 and 6 and in the embodiment of FIGS. 7 and 8, which better illustrate a housing face 18 having an opening 44 through which the shaft portion 42 of the rigid hub 40 extends. The disposable fluid pump 10c of FIGS. 5 and 6 and the disposable fluid pump 10d of FIGS. 7 and 8 may be provided in accordance with the preceding description of the disposable fluid pump 10a of FIGS. 1-3, with variations in the shape of the housing 14, the location of the inlet and outlet 26 and 28 (which are parallel, rather than being aligned or coaxial), and the shape of the impeller 22. Otherwise, the disposable fluid pump 10c of FIGS. 5 and 6 and the disposable fluid pump 10d of FIGS. 7 and 8 (along with the other disposable fluid pumps described herein, unless shown and/or stated to the contrary) are configured and operate as described above with respect to the embodiment of FIGS. 1-3.

Figure 6:
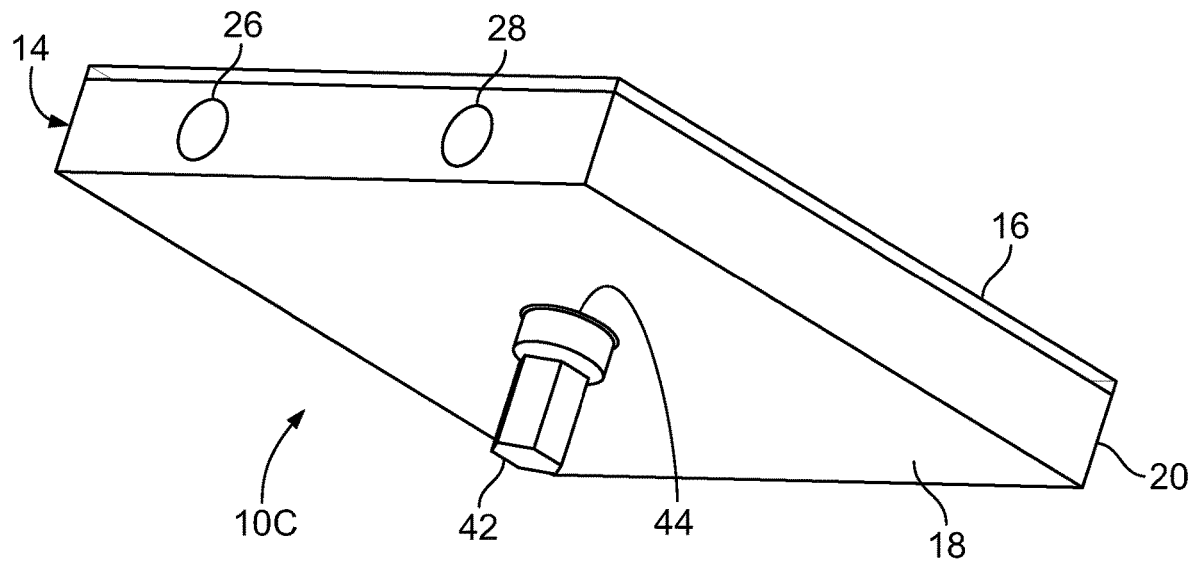

The shaft portion 42 may be variously configured (e.g., with a circular profile or cross-sectional shape, as in FIG. 2, or with a non-circular profile or cross-sectional shape, as in FIG. 6) that is received by a mating socket (not illustrated) of a durable drive unit 12 (FIG. 1). When all or a portion of the shaft portion 42 positioned outside of the housing 14 is received by the socket of the drive unit 12, a motor of the drive unit 12 may be operated to rotate the socket, which in turn rotates the shaft portion 42 and, thus, the impeller 22 within the fluid pump housing 14. Accordingly, as described above, the operation of the motor of the drive unit 12 may be varied to vary the volumetric flow rate of fluid through the fluid pump 10.

Figure 9:
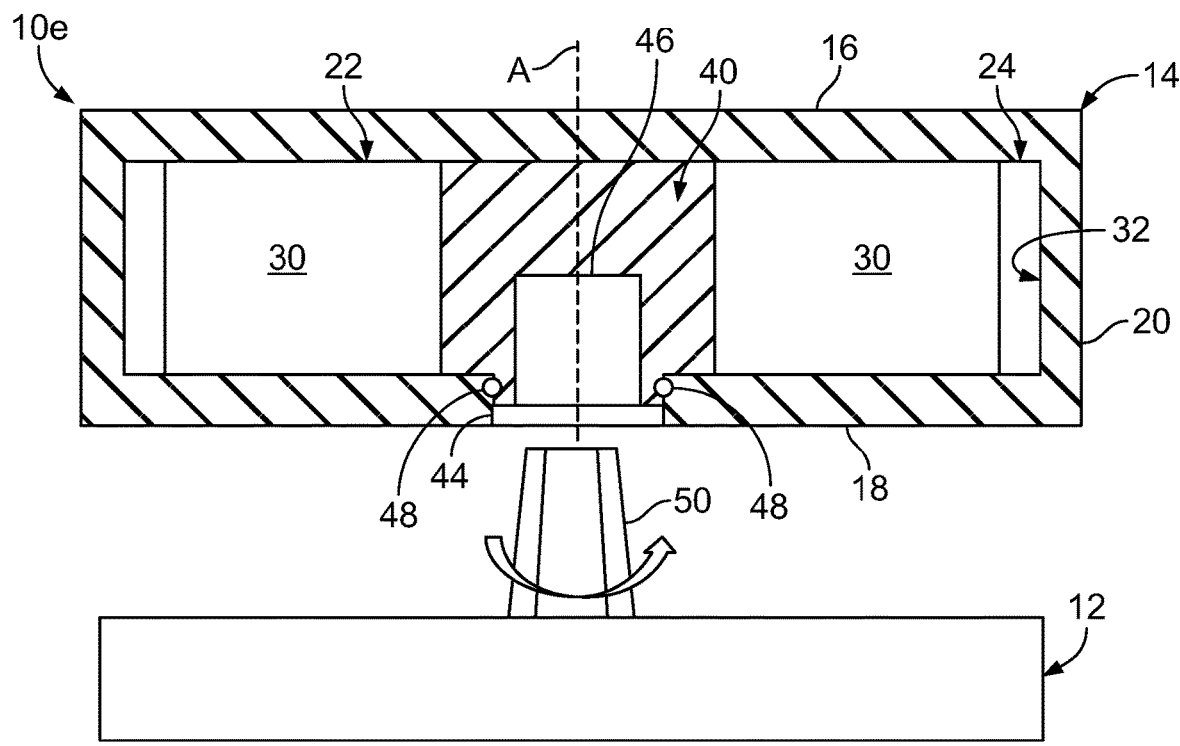
FIG. 9 is a cross-sectional view of another embodiment of a disposable fluid pump according to an aspect of the present disclosure.

Alternatively, the positions of the shaft portion and the socket may be reversed, with the rigid hub 40 of the impeller 22 defining a socket and the drive unit 12 including a shaft that is at least partially received by the socket. For example, FIG. 9 illustrates a disposable fluid pump 10e in which the rigid hub 40 of the impeller 22 defines a socket 46 that is accessible through an opening 44 in one of the housing faces 18. A seal 48 (e.g., an O-ring) may be positioned between the rigid hub 40 and the opening 44 of the housing face 18 to ensure a fluid-tight relationship while allowing rotation of the impeller 22 within the chamber 24. A similar seal 48 may also be employed in embodiments in which the rigid hub 40 of the impeller 22 includes a shaft portion 42. The durable drive unit 12 of FIG. 9 includes a shaft 50 that is at least partially received by the socket 46 of the rigid hub 40 when the fluid pump 10e has been mounted to the drive unit 12. The profile or cross-sectional shape of the socket 46 preferably matches or is complementary to the profile or cross-sectional shape of the mating shaft 50, such that rotation of the shaft 50 (by operation of a motor of the drive unit 12) causes rotation of the impeller 22 within the chamber 24 of the fluid pump 10e.

Figure 10:
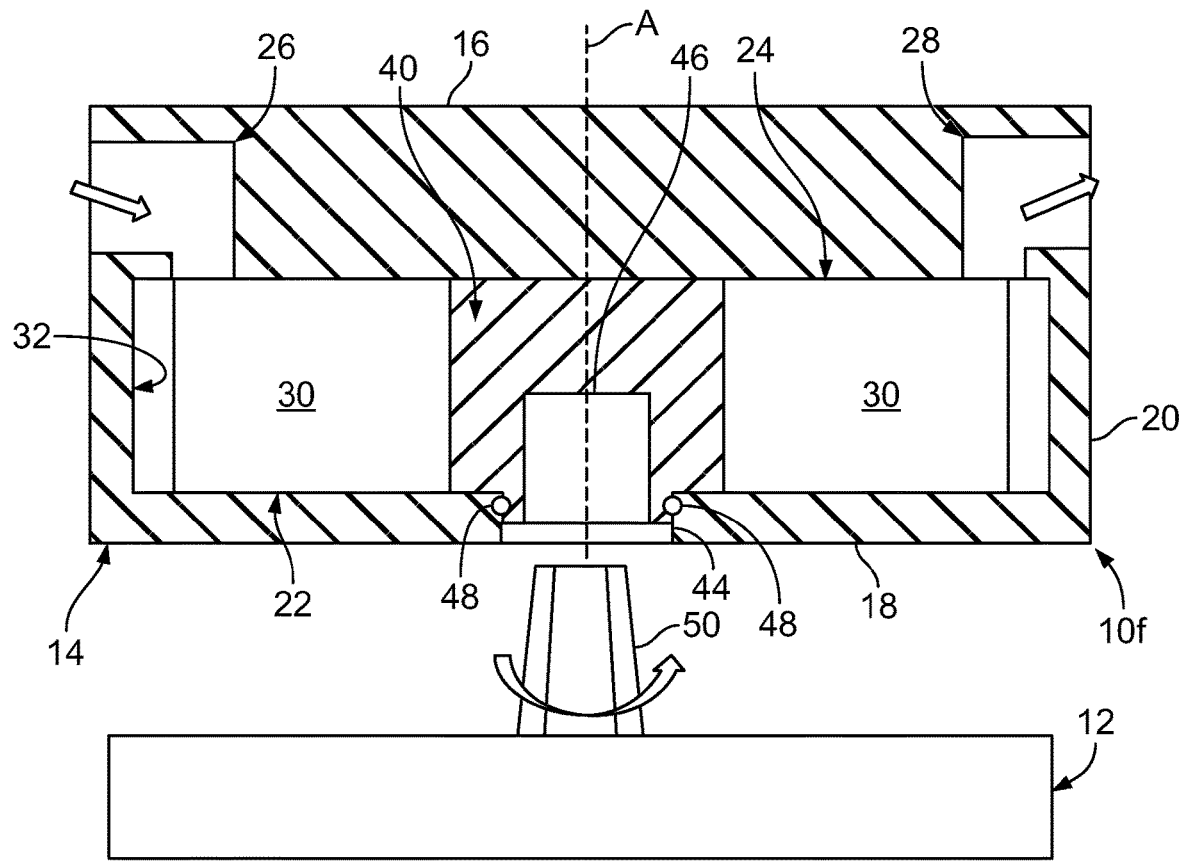
FIG. 10 is a cross-sectional view of another embodiment of a disposable fluid pump according to an aspect of the present disclosure.
Figure 11:
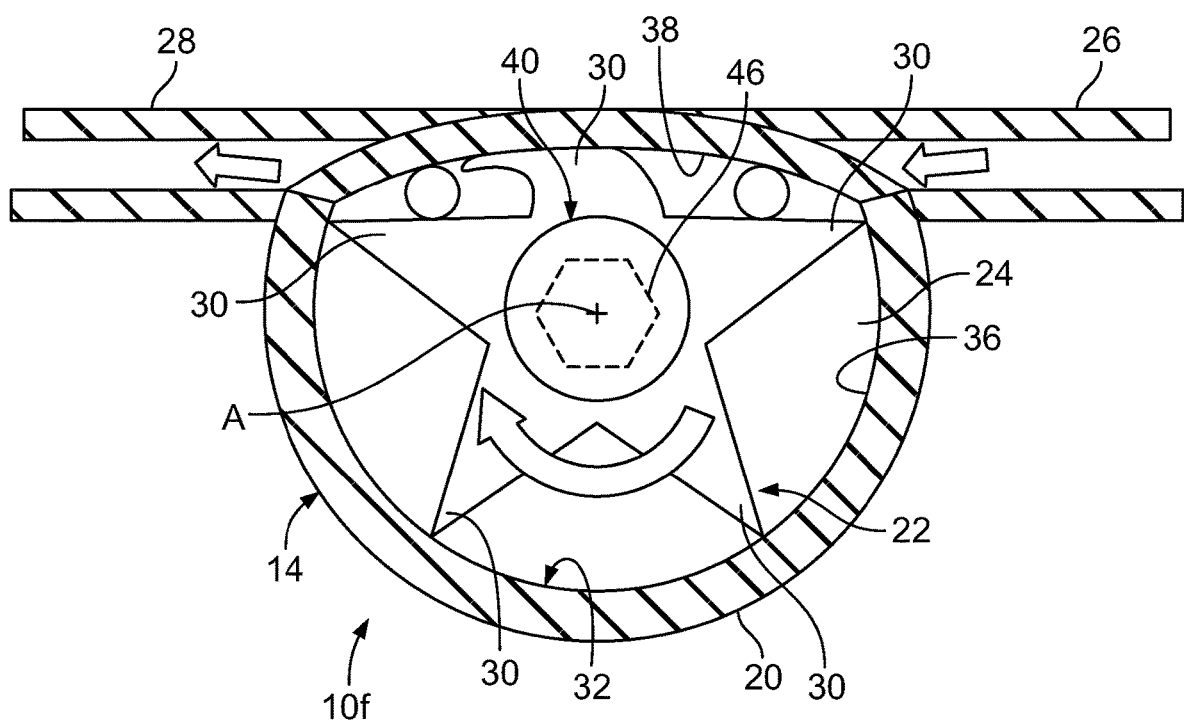
FIG. 11 is a diagrammatic plan view of the disposable fluid pump of FIG. 10, showing fluid flow into and out of the chamber of the disposable fluid pump.

The disposable fluid pump 10f of FIGS. 10 and 11 is a variation of the fluid pump 10e of FIG. 9. The disposable fluid pump 10f of FIGS. 10 and 11 is substantially identical to the fluid pump 10e of FIG. 9, except for the orientation of the inlet 26 and outlet 28. In the embodiment of FIG. 9 (as in the embodiments of FIGS. 1-8), the inlet 26 and outlet 28 are in the same plane as the impeller 22 and chamber 24 (which plane is substantially perpendicular to the rotational axis A). In contrast, in the embodiment of FIGS. 10 and 11, the housing 14 has an enlarged or extended sidewall 20, which increases the separation between the housing faces 16 and 18 without necessarily increasing the height of the chamber 24. By providing extra space between the housing faces 16 and 18, the inlet 26 and outlet 28 may each have not only a horizontal section (as in the embodiments of FIGS. 1-8), but also a vertical section that extends in a direction substantially parallel to the rotational axis A. By employing a vertical section that opens into the chamber 24, the inlet 26 and outlet 28 of FIGS. 10 and 11 extend through the sidewall 20 in a different plane than the plane that is occupied by the impeller 22 and the chamber 24.

A fluid pump 10f configured as in FIGS. 10 and 11 may be advantageous if the fluid pump 10f is to be partially received within a cavity or pocket of the associated drive unit, as making the inlet 26 and outlet 28 accessible in a different plane than the impeller 22 and chamber 24 may make it easier to connect the inlet 26 and outlet 28 to an external fluid flow path. It should be understood that the particular configuration of the inlet 26 and outlet 28 of FIGS. 10 and 11 is merely exemplary and that either or both may be differently configured without departing from the scope of the present disclosure. For example, rather than an inlet 26 or outlet 28 having horizontal and vertical sections that are substantially perpendicular to each other, the inlet 26 and/or outlet 28 could have an angled or diagonal section and/or a curved section or be otherwise configured in a way that makes the inlet 26 and/or outlet 28 accessible through the sidewall 20 in a different plane than one in which the impeller 22 and chamber 24 are present. In another variation, rather than extending between the chamber 24 and the sidewall 20, the inlet 26 and/or the outlet 28 may extend between the chamber 24 and one of the faces 16, 18 of the housing 14, with both extending through the same housing face 16, 18, one extending through the first face 16 and the other through the second face 18, or one extending through one of the faces 16, 18 and the other through the housing sidewall 20.

Turning back now to the mechanism or device that causes rotation of the impeller 22, while FIGS. 1-11 illustrate a physical interconnection between a shaft 42, 50 and socket 46 of the impeller 22 and the drive unit 12, other approaches are also contemplated by the present disclosure. For example, in one embodiment, the impeller 22 includes a magnetized portion or a portion formed of a ferromagnetic material. When used herein, the term "magnetized" or "magnetic" refers to either a substance or component that generates a magnetic field (e.g., a permanent magnet), while the term "ferromagnetic" refers to a material or substance or component that is attracted to a magnet when within the magnetic field generated by a magnetized member. The exact material composition of the magnetized or ferromagnetic portion of the impeller 22 may vary without departing from the scope of the present disclosure, being formed of iron or some other magnetizable substance or substances. It may be advantageous for all or a portion of the rigid hub 40 of the impeller 22 to be magnetized or formed of a ferromagnetic material, but it is also within the scope of the present disclosure for some other portion or portions of the impeller 22 to be magnetized or formed of a ferromagnetic material.

In embodiments in which the impeller 22 includes a magnetized or ferromagnetic portion, the drive unit 12 may also include a magnetized or ferromagnetic portion, which interacts with the magnetized or ferromagnetic portion of the impeller 22. In one embodiment, only one of the impeller 22 and the drive unit 12 includes a magnetized portion, while the other includes a portion formed of a ferromagnetic material. In another embodiment, both of the impeller 22 and the drive unit 12 include magnetized portions that are attracted to each other. With the impeller 22 and drive unit 12 magnetically coupled, the drive unit 12 may vary the magnetic field in the vicinity of the impeller 22 to cause the impeller 22 to rotate about the rotational axis A under the power of magnetism. If the impeller 22 is configured to interact with the drive unit 12 via magnetism, it may be preferred for the other components of the fluid pump 10 to be configured so as to be unaffected by the magnetized portion or portions of the impeller 22 and/or drive unit 12. For example, the fluid pump housing 14 may be formed of a plastic material that is neither attracted to nor repelled by a magnet in its presence.

By employing magnetism to rotate the impeller 22 within the chamber 24, it is possible to provide a pair of housing faces 16 and 18 that omit an opening 44 (to accommodate a shaft 42, 50 of the impeller 22 or drive unit 12). However, it is also within the scope of the present disclosure to employ magnetism in combination with a fluid pump 10 configured as in any of FIGS. 1-11 (i.e., with one of the impeller 22 and the drive unit 12 including a shaft 42, 50 that extends through an opening 44 in one of the housing faces 16, 18 to be at least partially received within a socket 46 of the other). In such embodiments, rather than relying upon a complementary, mating relationship between the shaft 42, 50 and socket 46 (or in combination with such a configuration), the socket 46 or shaft 42 of the impeller 22 is effectively held and rotated by magnetism applied via the matching portion of the drive unit 12.

Figure 12:
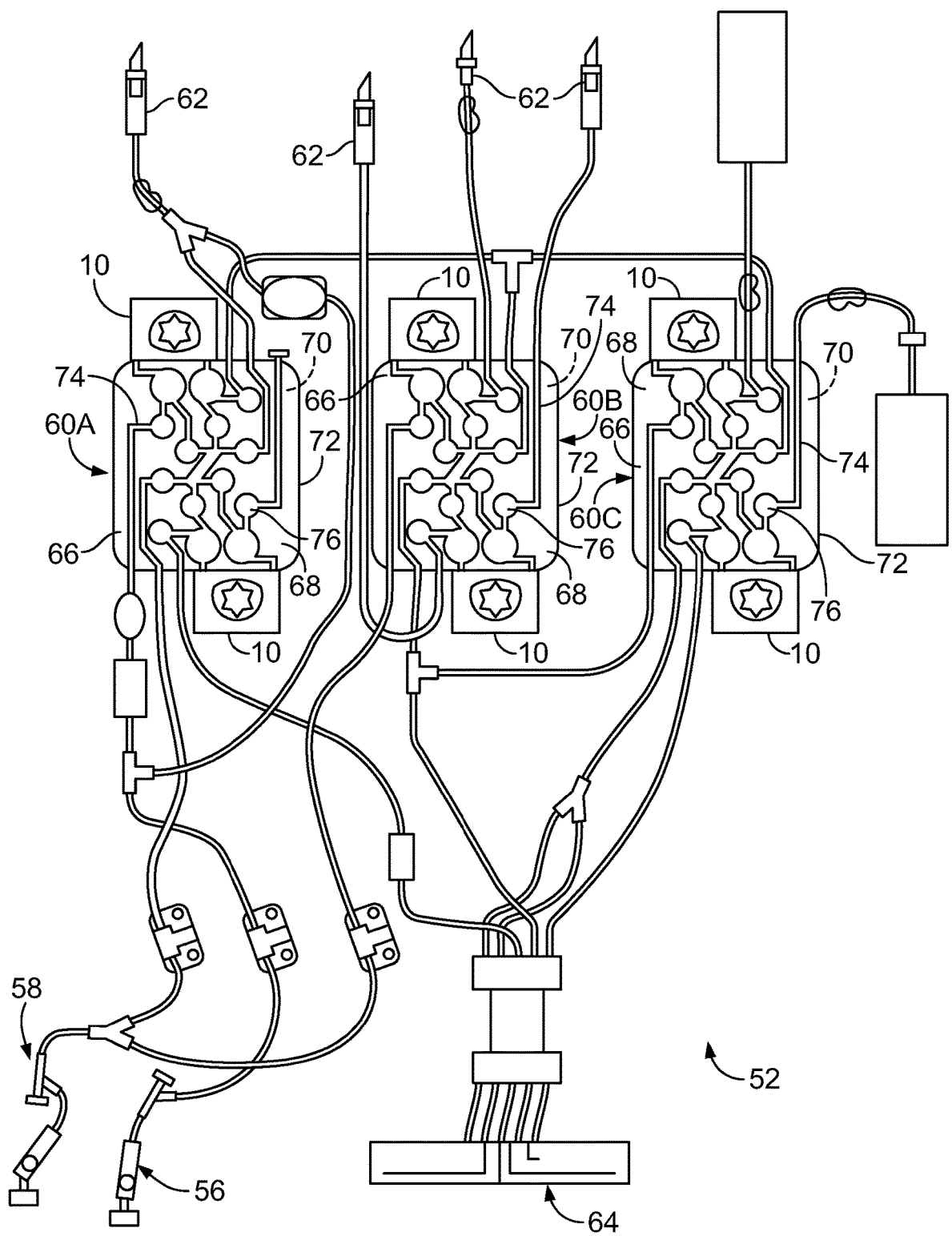
FIG. 12 is a plan view of an exemplary disposable fluid flow circuit incorporating a disposable fluid pump of the present disclosure.
Figure 13:
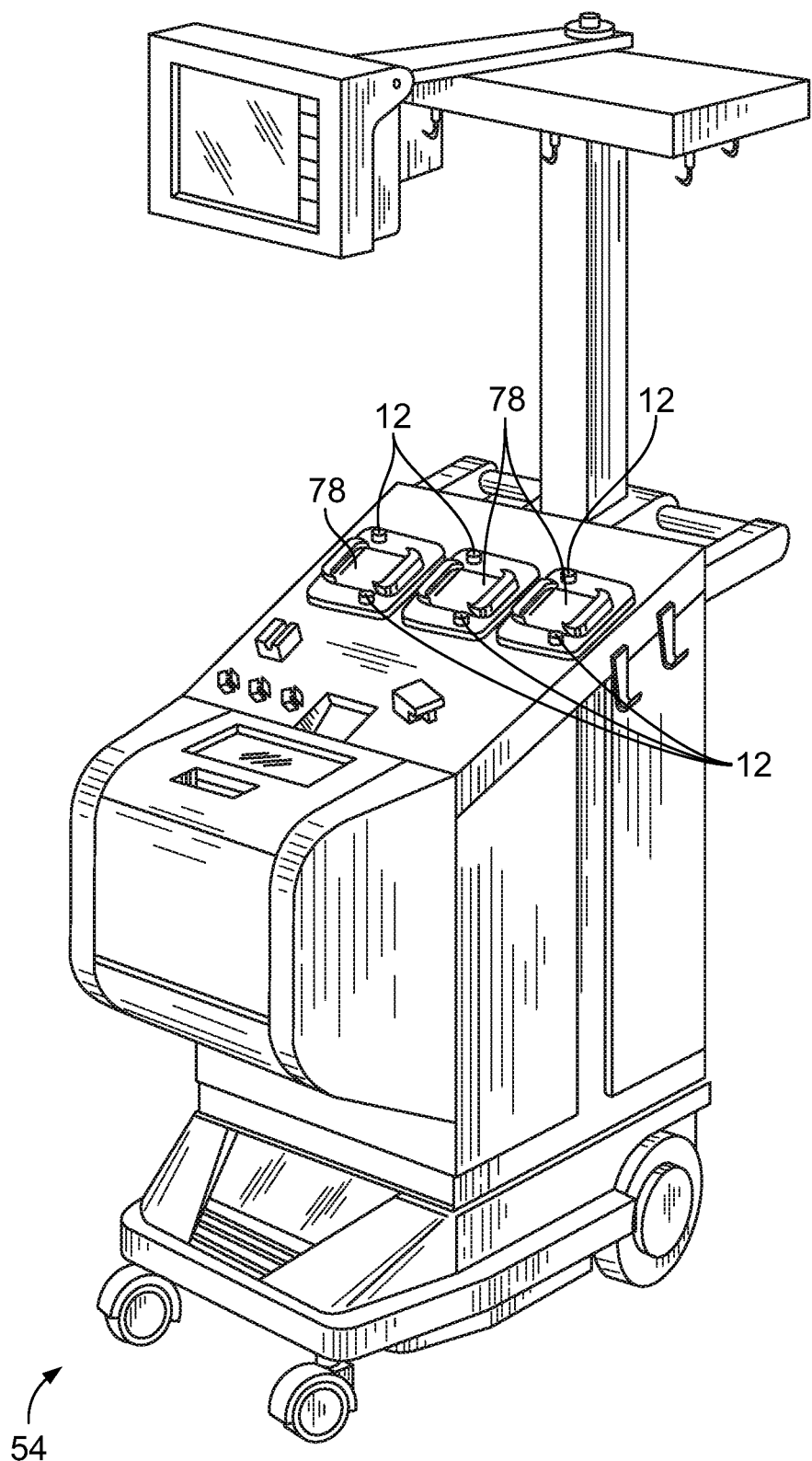
FIG. 13 is a perspective view of an exemplary durable hardware onto which the disposable fluid flow circuit of FIG. 12 may be mounted for processing a fluid.

Any of the fluid pumps described herein may be incorporated into disposable fluid flow circuits of the type having a plurality of components fluidly connected by fluid flow conduits (e.g., flexible plastic tubing). FIG. 12 shows an exemplary embodiment of a disposable fluid flow circuit 52 incorporating at least one disposable fluid pump 10, which may be used in combination with durable hardware 54 of the type shown in FIG. 13.

The illustrated fluid flow circuit 52 is a "two needle" system, which includes a pair of source access devices 56 and 58 (e.g., phlebotomy needles) for fluidly connecting a fluid source with the fluid flow circuit 52. The source access devices 56 and 58 are connected by tubing to a left cassette 60A, which will be described in greater detail herein. One of the source access devices 56 is used to draw fluid from the fluid source into the fluid flow circuit 52, while the other source access device 58 is used to return fluid to the fluid source. Various other access devices 62 may be connected to other conduits of the fluid flow circuit 52 to access containers from which fluid may be drawn (e.g., an anticoagulant fluid) and/or into which fluid may be conveyed (e.g., a separated fluid component). Other conduits of the fluid flow circuit 52 provide fluid communication with additional components of the fluid flow circuit 52, such as middle and right cassettes 60B and 60C and a processing chamber 64. The fluid flow circuit 52 of FIG. 12 is configured for use in separating blood into two or more components, but it should be understood that fluid flow circuits according to the present disclosure may be used for other purposes, in which case they may be differently configured and include different components in fluid communication with each other via the various conduits of the fluid flow circuit.

Each of the disposable cassettes (collectively referred to using the reference number 60) includes a body 66 (which may be a rigid, molded component) with a topside 68, an underside 70, and an edge wall 72 extending between the topside 68 and the underside 70. The body 66 defines a plurality of fluid flow paths 74, with fluid flow through the various fluid flow paths 74 being controlled by selectively actuating valve stations 76 also defined by the cassette body 66. The body 66 may define other structures or cavities, such as one or more sensor stations, which may be monitored to assess various characteristics of fluid flow through the cassette 60. The topside 68 and underside 70 may comprise covers or lids that seal the cavities of the body 66 from the outside environment, with the topside 68 being formed of a generally rigid material and the underside 70 comprising a flexible membrane or diaphragm in one embodiment. The edge wall 72 may comprise a formed perimeter edge of the cassette body 66 and, thus, be formed of a generally rigid material.

As shown in FIG. 12, at least one of the cassettes 60 may have a fluid pump 10 associated therewith and operable to move fluid through the fluid flow paths 74 of the cassette 60. In the illustrated embodiment, the three cassettes 60 are identical, with each having a pair of fluid pumps 10, but it is within the scope of the present disclosure for a single cassette to include only one associated fluid pump 10 or more than two fluid pumps 10 and/or for two cassettes of a single fluid flow circuit to be differently configured.

In the embodiment of FIG. 12, each fluid pump 10 is associated with the edge wall 72 of the associated cassette 60, with the inlet 26 and outlet 28 of each fluid pump 10 extending through the sidewall 20 of the fluid pump 10. In the embodiment of FIG. 12, the two fluid pumps 10 of a particular cassette 60 are associated with opposing ends of the edge wall 72, but it is within the scope of the present disclosure for a cassette 60 to be provided with a plurality of fluid pumps 10 associated with the same end of the edge wall 72 or with adjacent ends of the edge wall 72. Furthermore, it is also within the scope of the present disclosure for a fluid pump to be associated with the topside 68 or underside 70 of the cassette 60 if one or both of the inlet 26 and outlet 28 extend from the chamber 24 to one of the housing faces 16, 18.

In the embodiment of FIG. 12, a plurality of fluid flow paths 74 of the cassette 60 extend through the edge wall 72 of the cassette 60, with each of the inlet 26 and outlet 28 of each fluid pump 10 opening into a different one of these fluid flow paths 74. The housing 14 of the fluid pump 10 may be an integrally formed portion of the cassette body 66, in which case the inlet/outlet and associate fluid flow path define two sections of a common channel. Alternatively, the fluid pump 10 may be separately provided and secured to the cassette 60, in which case the inlet 26 and outlet 28 are configured so as to be in alignment with the associated fluid flow path 74 of the cassette 60 when the fluid pump 10 has been secured to the cassette 60 (e.g., by an adhesive or the like).

The durable hardware 54 (FIG. 13) includes a surface or station 78 that may be accessed to place each fluid pump 10 of a separate fluid processing cassette 60 into operative engagement with an associated drive unit 12 of the hardware 54. The surface or station 78 may be referred to as a "cassette holder" and take any of a number of forms, such as a horizontal or inclined surface or panel onto which a cassette 60 may be placed and then held in place by clamps or clips or the like. In other embodiments, the cassette holder may be a vertical surface with a door or cover hingedly attached thereto. The door may be opened to place a cassette 60 against the vertical surface, with the door then being closed to hold the cassette 60 in place against the vertical surface. Any of a number of other configurations of a cassette holder are also possible and within the scope of the present disclosure. The exact configuration of the cassette holder depends on the configuration of the associated cassette, as the two are configured to form a matched pair, with the number and location of the valve actuators, sensor actuators, and drive units of the cassette holder corresponding to the number and location of the valve stations, sensor stations, and fluid pumps of the cassette. As described previously, the underside 70 of the cassette 60 may comprise a flexible diaphragm that is acted upon by the valve actuators and sensors of the cassette holder 78 to direct and monitor the flow of fluid through the cassette 60 during use. A more detailed description of the configuration and operation of a suitable cassette body 66 and cassette holder 78 may be found in U.S. Pat. No. 5,868,696.

In use, the disposable fluid flow circuit 52 is mounted to the durable hardware 54, with the cassettes 60 mounted to the appropriate cassette holders 78 so as to put the fluid pumps 10 in registration with the corresponding drive units 12 of the durable hardware 54. Under the command of a system controller, the durable hardware 54 selectively operates the drive units 12 to actuate the fluid pumps 10 (as described above) to cause fluid flow through the fluid flow paths 74 of the cassettes 60 and through the conduits of the fluid flow circuit 52. The system controller also operates the valve actuators and sensors of the cassette holders 78 to interact with the corresponding valve and sensor stations of the cassette 60 to direct the flow of fluid through the cassettes 60 and monitor the flow of fluid through the fluid flow paths 74, along with controlling the other components of the durable hardware 54 to carry out a fluid processing procedure (e.g., commanding a centrifuge to rotate the processing chamber 64 of the fluid flow circuit 52 to separate fluid into its constituents).

Figure 14:
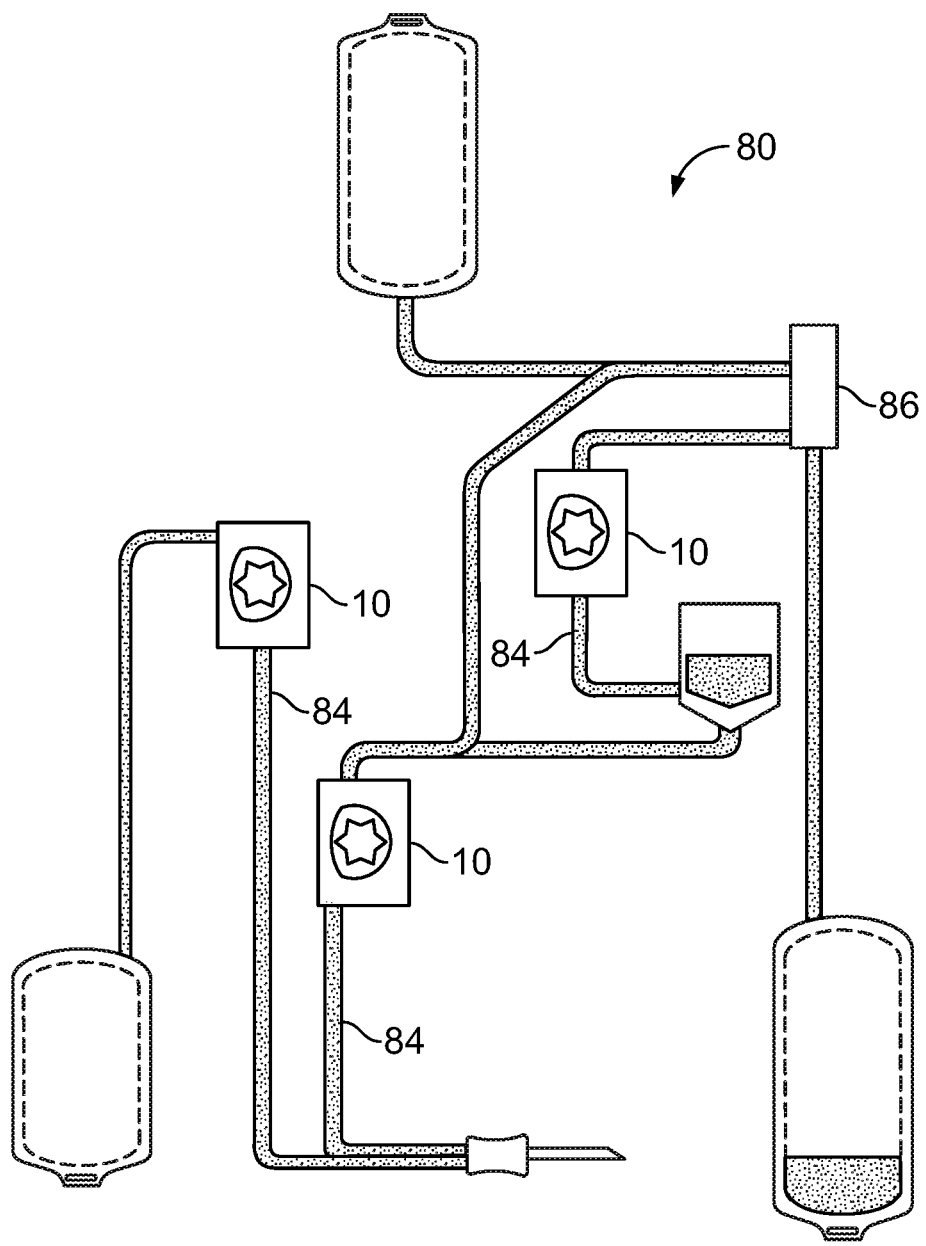
FIG. 14 is a diagrammatic view of another embodiment of an exemplary disposable fluid flow circuit incorporating a disposable fluid pump of the present disclosure.
Figure 15:
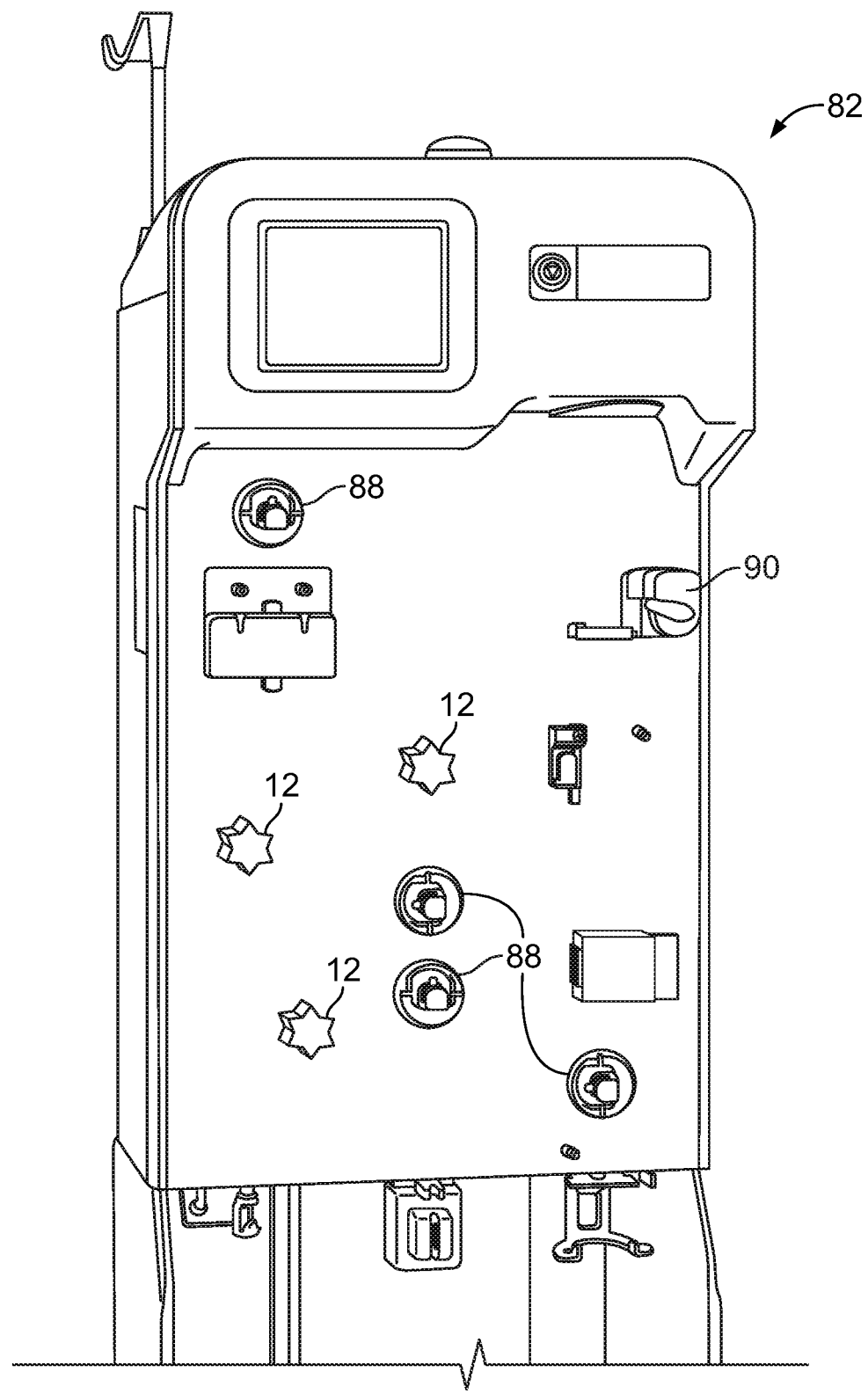
FIG. 15 is a perspective view of an exemplary durable hardware onto which the disposable fluid flow circuit of FIG. 14 may be mounted for processing a fluid.

FIG. 14 shows another embodiment of an exemplary disposable fluid flow circuit 80 incorporating at least one disposable fluid pump 10, which may be used in combination with durable hardware 82 of the type shown in FIG. 15. Other than the fluid flow circuit 80 of FIG. 14 being a "single needle" system (in contrast to the "two needle" system of FIG. 12), the principal difference between the fluid flow circuit 52 of FIG. 12 and the fluid flow circuit 80 of FIG. 14 is that the fluid flow circuit 80 of FIG. 14 omits cassettes. Instead, in the fluid flow circuit 80 of FIG. 14, the fluid flow pumps 10 are directly connected to the conduits 84 of the fluid flow circuit 80. In particular, a different fluid conduit 84 may be connected to each of the inlet 26 and outlet 28 of a fluid pump 10. For example, if the conduits 84 are provided as flexible tubing, then the end of a conduit 84 may be inserted within and secured to one of the inlet 26 and outlet 28 of a fluid pump 10 during assembly of the fluid flow circuit 80. Other methods of securing a fluid conduit 84 to the inlet 26 or outlet 28 of a fluid pump 10 (e.g., using a luer connector) may also be employed without departing from the scope of the present disclosure.

In use, the disposable fluid flow circuit 80 is mounted to the durable hardware 82, with the fluid pumps 10 in registration with the corresponding drive units 12 of the durable hardware 82. The other components of the fluid flow circuit 80 (e.g., a processing chamber 86) are associated with the corresponding components of the durable hardware 82. Under the command of a system controller, the durable hardware 82 selectively operates the drive units 12 to actuate the fluid pumps 10 to cause fluid flow through the fluid conduits 84 of the fluid flow circuit 80. The system controller also operates valves or clamps 88 of the durable hardware 82 (which may each accommodate a different conduit 84 of the fluid flow circuit 80) to properly direct the flow of fluid through the fluid flow circuit 80, along with controlling the other components of the durable hardware 82 to carry out a fluid processing procedure (e.g., commanding a rotor 90 to rotate a component of the processing chamber 86 of the fluid flow circuit 80 to separate fluid into its constituents).

Aspects of the present subject matter described above may be beneficial alone or in combination with one or more other aspects. Without limiting the foregoing description, in accordance with one aspect of the subject matter herein, there is provided a disposable fluid pump including a housing including first and second faces, with a sidewall extending therebetween. The housing defines a chamber and an inlet and outlet in fluid communication with the chamber. An impeller is rotatably mounted within the chamber and includes a plurality of flexible vanes.

In accordance with another aspect which may be used or combined with the immediately preceding aspect, the chamber has a non-uniform diameter.

In accordance with another aspect which may be used or combined with any of the preceding aspects, at least one of the inlet and outlet extends from the chamber to the sidewall of the housing.

In accordance with another aspect which may be used or combined with the immediately preceding aspect, the inlet and outlet extend from the chamber to the sidewall of the housing.

In accordance with another aspect which may be used or combined with any of the preceding aspects, the chamber and impeller are present in a plane, with at least one of the inlet and outlet extending from the chamber to the sidewall at a location within the same plane in which the chamber and the impeller are present.

In accordance with another aspect which may be used or combined with any of the first through fourth aspects, the chamber and impeller are present in a plane, with at least one of the inlet and outlet extending from the chamber to the sidewall at a location in a different plane than the same plane in which the chamber and the impeller are present.

In accordance with another aspect which may be used or combined with any of the preceding aspects, one of the first and second faces of the housing defines an opening. The impeller includes a rigid hub associated with the flexible vanes and defining a socket accessible through the opening and configured to receive a shaft for rotation of the impeller within the chamber.

In accordance with another aspect which may be used or combined with any of the first through sixth aspects, the impeller includes a rigid hub associated with the flexible vanes and defining a shaft portion. One of the first and second faces of the housing defines an opening through which the shaft portion of the rigid hub extends.

In accordance with another aspect which may be used or combined with any of the first through sixth aspects, the impeller includes a magnetized portion or a portion formed of a ferromagnetic material.

In accordance with another aspect, there is provided a disposable cassette adapted for incorporation into a disposable fluid flow circuit. The disposable cassette includes body having a topside, an underside, and an edge wall extending therebetween. The body defines a plurality of fluid flow paths. A fluid pump is associated with the body and includes a housing having first and second faces and a sidewall extending therebetween. The housing defines a chamber and an inlet and an outlet each in fluid communication with the chamber and with a different one of the fluid flow paths defined by the body of the cassette. An impeller is rotatably mounted within the chamber and includes a plurality of flexible vanes.

In accordance with another aspect which may be used or combined with the immediately preceding aspect, the housing of the fluid pump comprises an integrally formed portion of the body.

In accordance with another aspect which may be used or combined with any of the preceding two aspects, the chamber has a non-uniform diameter.

In accordance with another aspect which may be used or combined with any of the preceding three aspects, at least one of the inlet and outlet extends from the chamber to the sidewall of the housing.

In accordance with another aspect which may be used or combined with the immediately preceding aspect, the inlet and outlet extend from the chamber to the sidewall of the housing and are in fluid communication with the fluid flow paths defined by the body through the edge wall of the body.

In accordance with another aspect which may be used or combined with any of the preceding five aspects, the chamber and impeller are present in a plane. At least one of the inlet and outlet is in fluid communication with the fluid flow paths at a location within the same plane in which the chamber and the impeller are present.

In accordance with another aspect which may be used or combined with any of the tenth through fourteenth aspects, the chamber and the impeller are present in a plane. At least one of the inlet and outlet is in fluid communication with the fluid flow paths at a location in a different plane than the plane in which the chamber and the impeller are present.

In accordance with another aspect which may be used or combined with any of the preceding seven aspects, one of the first and second faces of the housing defines an opening. The impeller includes a rigid hub associated with the flexible vanes and defining a socket accessible through the opening and configured to receive a shaft for rotation of the impeller within the chamber.

In accordance with another aspect which may be used or combined with any of the tenth through sixteenth aspects, the impeller includes a rigid hub associated with the flexible vanes and defining a shaft portion. One of the first and second faces of the housing defines an opening through which the shaft portion of the rigid hub extends.

In accordance with another aspect which may be used or combined with any of the tenth through sixteenth aspects, the impeller includes a magnetized portion or a portion formed of a ferromagnetic material.

In accordance with another aspect, there is provided a disposable fluid flow circuit adapted for cooperative mounting on a durable hardware for processing a fluid. The disposable fluid flow circuit includes a plurality of fluid flow conduits and a fluid pump operable to convey fluid through at least a portion of the fluid flow circuit. The fluid pump includes a housing having first and second faces and a sidewall extending therebetween. The housing defines a chamber and an inlet and an outlet each in fluid communication with the chamber. An impeller is rotatably mounted within the chamber and includes a plurality of flexible vanes.

In accordance with another aspect which may be used or combined with the immediately preceding aspect, the chamber has a non-uniform diameter.

In accordance with another aspect which may be used or combined with any of the preceding two aspects, at least one of the inlet and outlet extends from the chamber to the sidewall of the housing.

In accordance with another aspect which may be used or combined with the immediately preceding aspect, the inlet and outlet extend from the chamber to the sidewall of the housing.

In accordance with another aspect which may be used or combined with any of the preceding four aspects, the chamber and the impeller are present in a plane. At least one of the inlet and outlet extends from the chamber to the sidewall at a location within the same plane in which the chamber and the impeller are present.

In accordance with another aspect which may be used or combined with any of the twentieth through twenty-third aspects, the chamber and the impeller are present in a plane. At least one of the inlet and outlet extends from the chamber to the sidewall at a location in a different plane than the plane in which the chamber and the impeller are present.

In accordance with another aspect which may be used or combined with any of the preceding six aspects, a cassette is connected to at least one of the fluid flow conduits and includes a body comprising a topside, an underside, and an edge wall extending therebetween. The body defines a plurality of fluid flow paths. The housing of the fluid pump is an integrally formed portion of the body, and the inlet and outlet of the fluid pump are in fluid communication with different fluid flow paths defined by the body through the edge wall of the body.

In accordance with another aspect which may be used or combined with any of the twentieth through twenty-fifth aspects, different fluid flow conduits are connected to the inlet and outlet through the sidewall of the housing.

In accordance with another aspect which may be used or combined with any of the preceding eight aspects, one of the first and second faces of the housing defines an opening. The impeller includes a rigid hub associated with the flexible vanes and defining a socket accessible through the opening and configured to receive a shaft for rotation of the impeller within the chamber.

In accordance with another aspect which may be used or combined with any of the twentieth through twenty-seventh aspects, the impeller includes a rigid hub associated with the flexible vanes and defining a shaft portion. One of the first and second faces of the housing defines an opening through which the shaft portion of the rigid hub extends.

In accordance with another aspect which may be used or combined with any of the twentieth through twenty-seventh aspects, the impeller includes a magnetized portion or a portion formed of a ferromagnetic material.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A disposable fluid pump comprising:
a housing including first and second faces and a sidewall extending between the first and second faces, the housing defining a chamber and an inlet and an outlet in fluid communication with the chamber; and
an impeller rotatably mounted within the chamber and including a plurality of flexible vanes, wherein
the impeller includes a rigid hub at least partially formed of a magnetized or ferromagnetic material, with the flexible vanes extending radially outwardly from the rigid hub,
the impeller and housing are configured for rotation of the impeller via magnetic field, and
the rigid hub does not include a shaft extending out of the housing.

2. The disposable fluid pump of claim 1, wherein
the chamber and the impeller are present in a plane, and
at least one of the inlet and outlet extends from the chamber to the sidewall at a location within the same plane in which the chamber and the impeller are present.

3. The disposable fluid pump of claim 1, wherein
the chamber and the impeller are present in a plane, and
at least one of the inlet and outlet extends from the chamber to the sidewall at a location in a different plane than the plane in which the chamber and the impeller are present.

4. The disposable fluid pump of claim 1, configured as a single-use item.

5. A disposable cassette adapted for incorporation into a disposable fluid flow circuit, the disposable cassette comprising:
a body including a topside, an underside, and an edge wall extending between the topside and the underside, the body defining a plurality of fluid flow paths and valve stations; and
a fluid pump associated with the body and comprising
a housing including first and second faces and a sidewall extending between the first and second faces, the housing defining a chamber and an inlet and an outlet each in fluid communication with the chamber and with a different one of the fluid flow paths defined by the body, and
an impeller rotatably mounted within the chamber and including
a rigid hub at least partially formed of a magnetized or ferromagnetic material, and
a plurality of flexible vanes extending radially outwardly from the rigid hub, wherein the rigid hub does not include a shaft extending out of the housing.

6. The disposable cassette of claim 5, wherein
the chamber and the impeller are present in a plane, and
at least one of the inlet and outlet is in fluid communication with said different fluid flow paths at a location within the same plane in which the chamber and the impeller are present.

7. The disposable cassette of claim 5, wherein
the chamber and the impeller are present in a plane, and
at least one of the inlet and outlet is in fluid communication with said different fluid flow paths at a location in a different plane than the plane in which the chamber and the impeller are present.

8. The disposable cassette of claim 5, wherein
one of the first and second faces of the housing defines an opening, and
the rigid hub defines a socket accessible through said opening and configured to receive a shaft for rotation of the impeller within the chamber.

9. The disposable cassette of claim 5, configured as a single-use item.

10. A disposable fluid flow circuit adapted for cooperative mounting on a durable hardware for processing a fluid, the disposable fluid flow circuit comprising:
a plurality of fluid flow conduits;
a fluid processing chamber in fluid communication with at least two of the fluid flow conduits;
at least one container in fluid communication with at least one of the fluid flow conduits and configured to receive at least a portion of a fluid; and
a plurality of fluid pumps each operable to convey fluid through at least a portion of the fluid flow circuit and comprising
a housing including first and second faces and a sidewall extending between the first and second faces, the housing defining a chamber and an inlet and an outlet each in fluid communication with the chamber and a different one of the fluid flow conduits, and
an impeller rotatably mounted within the chamber and including
a rigid hub at least partially formed of a magnetized or ferromagnetic material, and
a plurality of flexible vanes extending radially outwardly from the rigid hub, wherein the rigid hub does not include a shaft extending out of the housing.

11. The disposable fluid flow circuit of claim 10, wherein
the chamber and the impeller are present in a plane, and
at least one of the inlet and outlet extends from the chamber to the sidewall at a location within the same plane in which the chamber and the impeller are present.

12. The disposable fluid flow circuit of claim 10, wherein
the chamber and the impeller are present in a plane, and
at least one of the inlet and outlet extends from the chamber to the sidewall at a location in a different plane than the plane in which the chamber and the impeller are present.

13. The disposable fluid flow circuit of claim 10, further comprising a cassette connected to at least one of the fluid flow conduits and including a body comprising a topside, an underside, and an edge wall extending between the topside and the underside, the body defining a plurality of fluid flow paths, wherein
the housing of the fluid pump comprises an integrally formed portion of the body, and
the inlet and outlet are in fluid communication with different fluid flow paths defined by the body through the edge wall of the body.

14. The disposable fluid flow circuit of claim 10, wherein different fluid flow conduits are connected to the inlet and outlet through the sidewall of the housing.

15. The disposable fluid flow circuit of claim 10, wherein
one of the first and second faces of the housing defines an opening, and
the rigid hub defines a socket accessible through said opening and configured to receive a shaft for rotation of the impeller within the chamber.

16. The disposable fluid flow circuit of claim 10, configured as a single-use item.

17. The disposable fluid flow circuit of claim 10, wherein the fluid processing chamber comprises a biological fluid processing chamber, and
said at least one container is configured to receive at least a portion of a biological fluid and/or an additive fluid.

18. A disposable fluid pump comprising:
a housing including first and second faces and a sidewall extending between the first and second faces, the housing defining a chamber and an inlet and an outlet in fluid communication with the chamber; and
an impeller rotatably mounted within the chamber and including a plurality of flexible vanes, wherein
the chamber and the impeller are present in a plane, with the flexible vanes of the impeller being rotatable in the plane and with the inlet and the outlet extending from the chamber to the sidewall at locations within the plane, and
the first and second faces of the housing omit openings in fluid communication with the chamber.

19. A disposable cassette adapted for incorporation into a disposable fluid flow circuit, the disposable cassette comprising:
a body including a topside, an underside, and an edge wall extending between the topside and the underside, the body defining a plurality of fluid flow paths and valve stations; and
a fluid pump associated with the body and comprising
a housing including first and second faces and a sidewall extending between the first and second faces, the housing defining a chamber and an inlet and an outlet each in fluid communication with the chamber and with a different one of the fluid flow paths defined by the body, and
an impeller rotatably mounted within the chamber and including a plurality of flexible vanes, wherein the chamber and the impeller are present in a plane, with the flexible vanes of the impeller being rotatable in the plane and with the inlet and the outlet extending from the chamber to the sidewall at locations within the plane.

20. A disposable fluid flow circuit adapted for cooperative mounting on a durable hardware for processing a fluid, the disposable fluid flow circuit comprising:
a plurality of fluid flow conduits;
a fluid processing chamber in fluid communication with at least two of the fluid flow conduits;
at least one container in fluid communication with at least one of the fluid flow conduits and configured to receive at least a portion of a fluid; and
a plurality of fluid pumps each operable to convey fluid through at least a portion of the fluid flow circuit and comprising
a housing including first and second faces and a sidewall extending between the first and second faces, the housing defining a chamber and an inlet and an outlet each in fluid communication with the chamber and a different one of the fluid flow conduits, and
an impeller rotatably mounted within the chamber and including a plurality of flexible vanes, wherein the chamber and the impeller are present in a plane, with the flexible vanes of the impeller being rotatable in the plane and with the inlet and the outlet extending from the chamber to the sidewall at locations within the plane.

21. The disposable fluid flow circuit of claim 20, wherein the fluid processing chamber comprises a biological fluid processing chamber, and
said at least one container is configured to receive at least a portion of a biological fluid and/or an additive fluid.

* * * * *